United States Patent [19]
Oda et al.

[11] Patent Number: 4,996,158
[45] Date of Patent: Feb. 26, 1991

[54] OPTICAL RESOLUTION OF RACEMIC ALCOHOLS

[76] Inventors: Junichi Oda, 18, Shichiku Ushiwaka-cho, Kita-ku, Kyoto; Masaki Amano, 7-22, Higashiyama 2-chome, Chiba-ken, Kashiwa-shi; Haruhiko Toda, 15-1-118, Masago 2-chome, Chiba-ken, Chiba-shi; Toshiyuki Koyagi, 241, Kamihirama, Nakahara-ku, Kanagawa-ken, Kawasaki-shi, all of Japan

[21] Appl. No.: 287,043

[22] Filed: Dec. 21, 1988

[30] Foreign Application Priority Data

Dec. 26, 1987 [JP] Japan .................................. 62-330678
Mar. 16, 1988 [JP] Japan .................................. 63-60568

[51] Int. Cl.$^5$ .......................... C12P 7/02; C12P 7/62
[52] U.S. Cl. .................................. 435/280; 435/155; 435/135; 435/136
[58] Field of Search .................. 435/280, 18, 19, 23, 435/24, 135, 136, 155

[56] References Cited
FOREIGN PATENT DOCUMENTS
0080827 6/1983 European Pat. Off. .

OTHER PUBLICATIONS

Grant & Hackh's Chemical Dictionary, 1987, pp. 40 and 587.
Degueil-Castaing et al, Enzymatic Reactions in Organic Synthesis, 1987, pp. 953–954.
Chen, Quantitative Analyses of Biochemical Kinetic Resolution, 1987, pp. 2812–2817.
Cambou et al–J. Am. Chem. Soc., vol. 106 (1984), pp. 2687–2692.
Kirchner et al–J. Am. Chem. Soc., vol. 107 (1985), pp. 7072 to 7076.

Primary Examiner—Sam Rosen

[57] ABSTRACT

A racemic alcohol is subjected to the optical resolution by irreversibly esterifying one of the two antipodes of the racemic alcohol with an acid anhydride or enol ester of a carboxylic acid in a organic solvent in the presence of a hydrolase. This optical resolution uses a non-aqueous organic solvent in which the hydrolase is insoluble and involves an irreversible esterification, thus permitting an efficient optical resolution and improving recovery and re-usability of the hydrolase.

7 Claims, No Drawings

OPTICAL RESOLUTION OF RACEMIC ALCOHOLS

BACKGROUND OF THE INVENTION

The present invention relates to a method for resolving a racemic alcohol and, more particularly, to a method for resolving a racemic alcohol into its two antipodes using an enzymatic reaction in an organic solvent with high selectivity and efficiency.

Heretofore, as an optical resolution of a racemic alcohol via an esterification using an enzyme are known a process for reacting a racemic alcohol with a carboxylic acid, that is, a process using a so-called esterification, a process using an interesterification between a racemic alcohol and a carboxylic acid ester, and so on.

Since it is difficult to carry out the process using the esterification in an aqueous system because a hydrolysis of an ester formed occurs predominantly, it is reported that it is carried out in an organic solvent [J. Am. Chem. Soc., 107, 7072 (1985)]. In this example, however, it is reported that a gel substance is formed as a result of dissolution of an organic solvent-insoluble enzyme in water formed in the system, thereby leading to an insufficient recovery of the enzyme after the completion of the reaction. It further suffers from the disadvantages that the reaction proceeds slowly and that a yield and a purity of an optically active substance are not always sufficient. Accordingly, a reaction such as using an organic solvent-insoluble enzyme in an organic solvent is said to be inappropriate. The interesterification as another process for the optical resolution of the racemic alcohol may be represented in the following reaction scheme:

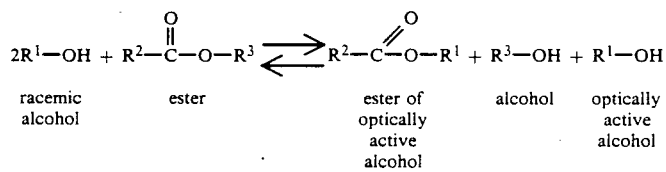

wherein
$R^1$ and $R^3$ each is a residue of an alcohol, and
$R^2$ is a residue of a carboxylic acid.

As this reaction is an equilibrium reaction, it is extremely difficult to thoroughly convert the starting material to the reaction product so that this interesterification suffers from the disadvantage that a reaction takes a long period of time.

This tendency arises to an increased extent in instances where a secondary alcohol or a tertiary alcohol, each having a large degree of a steric hindrance, is used as a racemic alcohol.

In order to overcome these disadvantages, processes have been proposed in which there are used an ester such as a trihaloethanol ester having a large steric hindrance, alcohol moiety [(J. Am. Chem.: 107, 7072 (1985); Tetrahedron Letters: 28, 2091 (1987)] and a diacylglycerin ester, [Tetrahedron Letters: 27, 29 (1986)]. These processes present the advantage that the interesterification can proceed to some extent toward the right side in the above reaction scheme, however, they still require long reaction times. In particular, in instances where the racemic alcohol is the secondary or tertiary alcohol, this process still suffers from the advantages that a degree of the completion of the reaction is insufficient and that the corresponding optically active product cannot be synthesized efficiently.

Heretofore, the esterification of an alcohol with an acid anhydride using a catalyst such as an acid or a base without the use of any enzyme is known. However, this type of reaction is substantially infeasible to control a stereo selectively of a chemical product. There are disclosed an example using an open-chain acid anhydride [W. W. Prichard: Org. Syn. Coll., Vol. 3, 452 (1955)] and an example using a cyclic acid anhydride [A. C. Cope.: Org. Syn., Coll.: Vol. 4, 304 (1963)].

In a conventional reaction system using an enzyme as a catalyst, it is extremely disadvantageous to carry out the esterification because the acid anhydride that is an acylating agent undergoes the hydrolysis due to water in the system using a water-soluble enzyme in an aqueous solution and the acylating agent is converted to the free carboxylic acid.

Furthermore, as an example of synthesizing an ester by means of the interesterification with an enol ester of a carboxylic acid utilizing an irreversible reaction, there is known an acylation of an alcohol with isopropenyl acetate using as a catalyst a strong acid such as p-toluenesulfonic acid or sulfuric acid [Ind. Eng. Chem.: 41(12), 2920(1949)]. This method requires severe conditions for reaction so that an unstable substance cannot be used as a starting material and it is extremely difficult to use this method for synthesizing an optically active substance.

SUMMARY OF THE INVENTION

Therefore, an object of the present invention is to provide a method of resolving a racemic alcohol into its two antipodes, which permits an optical resolution of the racemic alcohol with high yield and in a short reaction time unlike conventional techniques, and furthermore which is extremely advantageous for the optical resolution of the racemic alcohol on the industrial scale because it is superior in recovery and reusability of the enzyme used.

The present invention has one of the features that a non-aqueous organic solvent which hardly dissolves the enzyme is used as a reaction solvent in order to improve the recovery and reusability of the enzyme and that the irreversible esterification using the acid anhydride or the enol ester of the carboxylic acid as an esterifying agent is adopted in order to allow the racemic resolution to be carried out in an efficient way.

In accordance with the present invention, there is provided a method for resolving a racemic alcohol into its two antipodes, comprising the steps of reacting the racemic alcohol with an esterifying agent selected from an acid anhydride and an enol ester of a carboxylic acid in an organic solvent in the presence of a hydrolase to esterify one of the antipodes of the racemic alcohol with the esterifying agent, so that a reaction mixture containing the esterified antipode and unreacted antipode is formed; and separating either the esterified antipode or unreacted antipode from the reaction mixture.

Other objects, features and advantages of the invention will become apparent from the detailed description of the preferred embodiments of the invention to follow.

DETAILED DESCRIPTION OF THE PREFERRED EMBODIMENTS

In the method of the present invention, the racemic alcohol is first esterified irreversibly with the esterifying agent selected from an acid anhydride and an enol ester of a carboxylic acid.

The esterification using, for example, an open-chain acid anhydride such as butyric anhydride as the esterifying agent may be represented in the following reaction scheme:

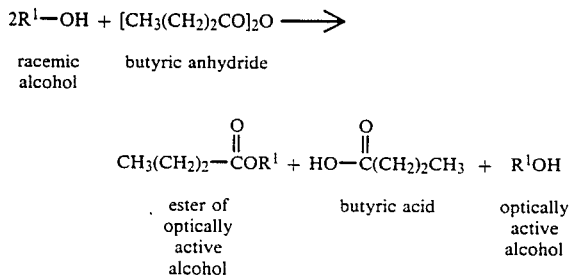

wherein $R^1$ is a residue of an alcohol.

The esterification using, for example, a cyclic acid anhydride such as glutaric anhydride as the esterifying agent may be represented in the following reaction scheme:

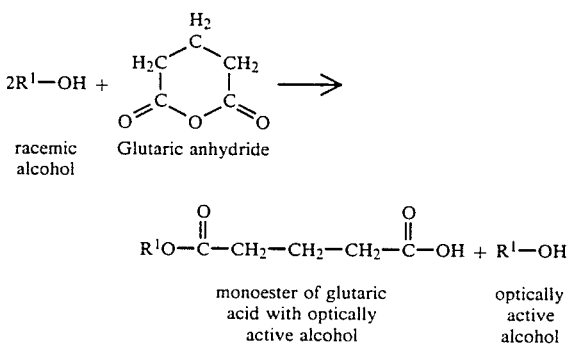

wherein $R^1$ is a residue of an alcohol.

In another aspect of the present invention, the reaction using, for example, isopropenyl acetate as the enol ester of carboxylic acid may be represented as follows:

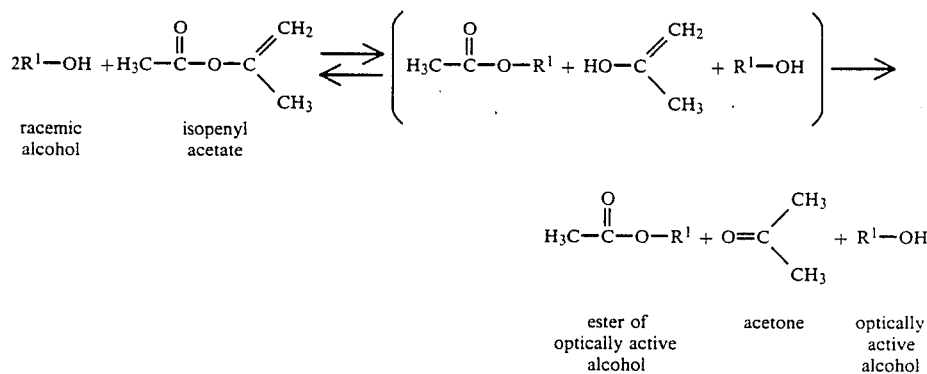

wherein $R^1$ is a residue of an alcohol.

In one aspect of the present invention, the reaction using the open-chain or cyclic acid anhydride utilizes an irreversible reaction involving the cleavage of the acid anhydride so that. unlike conventional interesterification which involves an equilibrium reaction (reversible reaction), the reaction proceeds to the right irreversibly as have been described above, thus completing the reaction in a short time and providing an optically active product efficiently.

Although the acid anhydride to be used for the present invention may be of an open-chain or cylic structure, it is not desirable to use such an acid anhydride as being so reactive to allow the reaction to proceed in a non-enzymatic manner. From the foregoing, it is preferred to use a straight-chained or branched chained symmetric acid anhydride having carbon atoms of 8 or more as the open-chain acid anhydride. As the cyclic acid anhydride it is preferred to use a 5-membered or 6-membered cyclic acid anhydride such as, for example, succinic anhydride, maleic anhydride, phthalic anhydride, glutaric anhydride, 3-methylglutaric anhydride, 2,4-dimethylglutaric anhydride or the like.

In another aspect of the present invention, the isopropenyl group of isopropenyl acetate used as the enol ester of carboxylic acid is converted into acetone after acylating the racemic alcohol. In this case, the acetone does not undergo the acylation in the reaction system so that, unlike conventional interesterification involving an equilibrium reaction (reversible reaction), the reaction proceeds thoroughly to the right in the above reaction scheme in an irreversible manner, thus completing the reaction in a short period of time and permitting an efficient production of an optically active product.

It is further to be noted that acetone formed during the reaction is a solvent which is used usually for purification of an enzyme so that it does not exert any adverse influence upon the enzyme in the reaction system.

The enol ester of the carboxylic acid to be used in another aspect according to the present invention may be a condensed ester of an aliphatic carboxylic acid with an enol-type alcohol. The aliphatic carboxylic acid may include an aliphatic acid having carbon atoms of 1 to 8, such as, for example, acetic acid, propionic acid, butyric acid or the like. The enol-type alcohol may include, for example, vinyl alcohol, isopropenyl alcohol or the like. Although any condensed ester may be used for the method according to the present invention, it is preferred to select one from the viewpoint of readiness in availability and synthesis. Such a condensed ester may include, for example, isopropenyl acetate, vinyl acetate, vinyl butyrate or the like.

In accordance with the method of the present invention, although there is no limitation to the kind of the racemic alcohol, it is preferred to use a secondary alcohol rather than a primary alcohol, such as solketal, glysidol or 2,3-dichloropropanol, because the former permits a better recognition of an enantiomer than the latter. As examples of the secondary alcohols may be enumerated a derivative of an aliphatic secondary alcohol such as, for example, (R,S)-3-chloro-1-p-toluenesulfonyloxy-2-propanol, (R,S)-1-phenyl-ethanol, (R,S)-1-phenyl-2-chloroethanol, (R,S)-mandelonitrile or the like, an aliphatic secondary alcohol such as, for example, 2-heptanol, 2-octanol, 2-nonanol, 2-decanol or the like, a racemic alcohol having plural hydroxyl groups such as phenylethylene glycol, or the like.

As an organic solvent to be used for the method in accordance with the present invention may be used any inert non-aqueous organic solvent. Suitable non-aqueous organic solvents may include, for example, a straight-chained hydrocarbon such as n-heptane, n-hexane or the like, a branch-chained hydrocarbon such as isobutane, isopentane, 2-methylpentane or the like, an alicyclic hydrocarbon such as cyclopentane, cyclohexane or the like, a halogenated hydrocarbon such as methylene dichloride, chloroform, carbon tetrachloride, dichloroethane, trichloroethane or the like, an aromatic hydrocarbon such as benzene, toluene, xylene, cumene, cymene, mesitylene, diisopropylbenzene or the like, and aliphatic ether such as diethyl ether, diisopropyl ether, di-n-butyl ether or the like, and an alicyclic ether such as tetrahydrofuran, tetrahydropyran or the like. Among those organic solvents as have been enumerated hereinabove, n-hexane, toluene, diisopropyl benzene, diethyl ether, diisopropyl ether, di-n-butyl ether, carbon tetrachloride are preferred.

An enzyme to be used for the method according to the present invention may be a hydrolase including lipases such as, for example, porcine pancreas lipase, a yeast lipase originated from genus Candida, a mycelial lipase originated from genuses Aspergillus, Mucor or Pseudomonas, esterases originated from porcine liver, and proteases such as trypsin, chymotripsin or the like. The hydrolase may be used in a purified form or in a crude form, and may be in such a form as powder, granules or the like. There may also be used dry products of hydrolase-forming cells such as processed, resting and static cells.

The hydrolase may also be used in a form in which it is immobilized by means of the physical adsorption method on a carrier including a polymer such as, for example, polystyrene, polypropylene, starch or glutene, or an inorganic material such as, for example, activated carbon, porous glass, cerite, zeolite, caolinite, bentonite, alumina, silica gel, hydroxyl apatite, calcium phosphate or metal hydroxide, or the like. The enzyme recovered from the reaction mixture by means of filtration after the completion of the reaction may be re-used because it still retains its sufficient activity and steric selectivity, and an enzyme for use for continuous reaction may also be used.

In accordance with the present invention, it is necessary to reduce a water content in the reaction system to the least possible level so that the reaction is carried out in a substantially non-aqueous system. On the other hand, it is also important that at least a quanity of water should be present in the reaction system in order for the hydrolase to properly function. Thus, it is preferred that the liquid phase of the reaction system, composed of the acid anhydride or carboxylic acid enol ester, the alcohol and the organic solvent, have a water content of 2% (w/v) or less, more preferably 0.5% (w/v) or less. The water content of the solid phase of the reaction system, composed of the enzyme powder or granules, is from 0.1% to 10% (w/v), preferably from 0.5% to 5% (w/v). The water content of each material may be adjusted by various drying methods such as using an appropriate type of a dehydrating agent, e.g., molecular sieves, in the case of liquids and using a vacuum desiccator in the case of solids.

The molar ratio of the racemic alcohol to be used as the reaction substrate according to the present invention to the esterifying agent (i.e., acid anhydride or the enol ester of the carboxylic acid) is preferably at least 2:1.

An optically active substance, that is, an optically active ester or alcohol, may be separated from reaction products subsequent to the esterification or interesterification. For this purpose, there may be employed extraction using a two phase system using an organic solvent soluble sparingly in water or a non-aqueous organic solvent, separation by a column, separation by distillation, and so on. In particular, when the cyclic acid anhydride is used, there may also be used extraction operation using an aqueous alkaline solution and a water-insoluble organic solvent and the use of an ion exchange resin or the like.

The method according to the present invention provides the remarkable advantages that it permits the optical resolution of the racemic alcohol in an irreversible manner as have been shown hereinabove, thus producing an optically active substance in a short period of time and in efficient way, that it permits the ready and easy optical resolution of the optically active substance even using a secondary or tertiary alcohol as the racemic alcohol which conventionally requires a long period of time for reaction and which blocks the reaction on account of its steric hindrance, and that the reaction is carrried out in an organic solvent so that no enzyme is dissolved in the reaction system, thus enabling the enzyme and the reaction product to be separated and recovered from the reaction system by means of simple operation such as filtration or the like and allowing the recovered enzyme to be re-used without further processing.

Accordingly, the present invention is extremely useful for the method of the manufacture of an optically active intermediate substance for pharmaceuticals such as β-blocker effective for an anti-arrythmia or a hypotensive agent, or for electronic material such as a ferroelectric liquid crystal.

The following examples will further illustrate the present invention.

EXAMPLE 1

(R, S)-1-Phenylethanol (1.26 grams, 10.3 mmol) and glutaric anhydride (0.645 grams, 5.7 mmol) were dissolved in 50 ml of toluene dried in advance on Molecular Sieve 4A for one day. To the resultant solution was added 5 grams of hydrolase (Amano P: product of Amano Seiyaku K. K.), and the resulting mixture was stirred at 25° C. and 150 r.p.m. After 16 hours, the reaction mixture was fitered, and the filtrate was subjected to high performance liquid chromatography (HPLC)

using an optically active column and found to contain (S)-1-phenylethanol in an optical purity of 90% with a theoretical yield of 85%.

EXAMPLE 2

(R, S)-3-Chloro-1-p-toluenesulfonyloxy-2-propanol (1 gram, 3.78 mmol) and succinic anhydride (0.21 gram, 2.10 mmol) were dissolved in 10 ml of carbon tetrachloride dried in advance on Molecular Sieve 4A for one day. To the resulting solution was added 1 gram of a hydrolase (Amano CES: Product of Amano Seiyaku K. K.), and the mixture was stirred at 25° C. and 150 r.p.m. for 16 hours. The reaction mixture was filtered, and the filtrate was subjected to HPLC using an optically active column. It was found that there was obtained (R)-3-chloro-1-p-toluenesulfonyl-2-propanol in an optical purity of 95% with a theoretical yield of 80%.

EXAMPLE 3

(R, S)-1-Phenyl-1-chloroethanol (0.626 gram, 4.0 mmol) and phthalic anhydride (0.33 gram, 2.22 mmol) were dissolved in 5 ml of diethyl ether dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 16 hours. The reaction mixture was filtered, and the filtrate was subjected to HPLC using an optically active column. There were obtained (R)-1-phenyl-2-chloroethanol in an optical purity of 92% with a theoretical yield of 70% and its S-ester in an optical purity of 96% with a theoretical yield of 80%.

EXAMPLE 4

(R, S)-Mandelonitrile (1.07 grams, 8.0 mmol) and glutaric anhydride (0.5 gram, 4.4 mmol) were dissolved in 10 ml of carbon tetrachloride dried in advance on Molecular Sieve 4A for one day. To the resulting solution was added 2 grams of an enzyme (Amano P: Product of Amano Seiyaku K. K.), and the mixture was stirred at 25° C. and 150 5.p.m. for 16 hours. The reaction mixture was filtered, and the filtrate was subjected to HPLC using an optically active column. Mandelonitrile was obtained in an optical purity of 90% with a theoretical yield of 78%.

EXAMPLE 5

(R, S)-3-Chloro-1-p-toluenesulfonyloxy-2-propanol (1 gram, 3.78 mmol) and hexanoic anhydride (0.446 gram, 2.08 mmol) were dissolved in 10 ml of carbon tetrachloride dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 8 hours. The reaction mixture was filtered, and the filtrate was subjected to HPLC using an optically active column. It was found that (R)-3-chloro-1-p-toluenesulfonyl-oxy-2-propanol was obtained in an optical purity of 95% with a theoretical yield of 80%.

EXAMPLE 6

(R, S)-2-Octanol (2.6 grams, 20.0 mmol) and glutaric anhydride (1.254 grams, 11.0 mmol) were dissolved in 50 ml of carbon tetrachloride dried in advance on Molecular Sieve 4A for one day. To the resulting solution was added 5 grams of porcine pancreas lipase (Product of Sigma), and the mixture was stirred at 25° C. and 150 r.p.m. for 16 hours. The reaction mixture was filtered, and the filtrate was subjected to HPLC using an optically active column. It was found that there was obtained substantially the same result as in Example 1.

EXAMPLE 7

(R, S)-3-Chloro-1-p-toluenesulfonyloxy-2-propanol (1 gram, 3.78 mmol) and isopropenyl acetate (0.76 gram, 7.56 mmol) were dissolved in 5 ml of carbon tetrachloride dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 8 hours. The reaction mixture was filtered, and the filtrate was subjected to HPLC using an optically active column. (R)-3-chloro-1-p-toluenesulfonyl-oxy-2-propanol was obtained in an optical purity of 100% with a theoretical yield of 100%.

Using the enzyme recovered by filtration, the reaction was repeated in the same reaction conditions and found to give substantially the same results as obtained immediately hereinabove.

EXAMPLE 8

(R, S)-1-Phenylethanol (0.244 gram, 2 mmol) and isopropenyl acetate (0.2 gram, 2 mmol) were dissolved in 10 ml of n-hexane dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 4 hours. The reaction mixture was filtered, and the filtrate was subjected to HPLC using an optically active column. (S)-1-phenylethanol was obtained in an optical purity of 100% with a theoretical yield of 100%.

EXAMPLE 9

(R, S)-1-Phenyl-2-chloroethanol (0.626 gram, 4.0 mmol) and isopropenyl acetate (0.80 gram, 8.0 mmol) were dissolved in 40 ml of diisopropyl ether dried in advance on Molecular Sieve 4A for one day. To the resulting solution was added 2 grams of an enzyme (Amano P: Product of Amano Seiyaku K. K.), and the mixture was stirred at 25° C. and 150 r.p.m. for 10 hours. The reaction mixture was filtered, and the filtrate was subjected to HPLC using an optically active column. (R)-1-chloroethanol was obtained in an optical purity of 92% with a theoretical yield of 100% and (S)-acetyl product was obtained in an optical purity of 96% with a theoretical yield of 100%.

EXAMPLE 10

(R, S)-Mandelonitrile (1.07 grams, 8.0 mmol) and isopropenyl acetate (1.6 gram, 16.0 mmol) were dissolved in 40 ml of diisopropyl ether dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 8 hours. The reaction mixture was filtered, and the filtrate was subjected to HPLC using an optically active column. Mandelonitrile was obtained in an optical purity of 100% with a theoretical yield of 78%.

EXAMPLE 11

(R, S)-1-Phenyl-1,2-ethane diol (1 gram, 7.2 mmol) and isopropenyl acetate (2.88 grams, 28.8 mmol) were dissolved in 5 ml of carbon tetrachloride dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 8 hours. The reaction mixture was filtered, and the filtrate was subjected to HPLC using an optically active column. 2-acetoxy-1-phenyl-ethanol was obtained in an optical purity of 100% with a theoretical yield of 70%.

EXAMPLE 12

(R, S)-2-Octanol (2.6 grams, 20.0 mmol) and isopropenyl acetate (4.0 grams, 40.0 mmol) were dissolvled in 200 ml of hexane dried in advance on Molecular Sieve 4A for one day. To the resulting solution was added 10 grams of an enzyme (Amano P: Product of Amano Seiyaku K. K.), and the mixture was stirred at 25° C. and 150 r.p.m. for 8 hours. The reaction mixture was filtered, and the filtrate was subjected to separation of 2-octanol and 2-octyl acetate. The polarimetric analysis gave substantially the same results as obtained in Example 7.

EXAMPLE 13

(R, S)-2-Decanol (3.2 grams, 20.0 mmol) and isopropenyl acetate (0.76 gram, 7.56 mmol) were dissolved in 200 ml of hexane dried in advance on Molecular Sieve 4A for one day. To the resulting solution was added 10 grams of an enzyme (Amano CES: Product of Amano Seiyaku K. K.), and the mixture was stirred at 25° C. and 150 r.p.m. for 8 hours. The reaction mixture was filtered, and decanol and 2-decanyl acetate were separated from the filtrate. The polarimetric analysis gave substantially the same results as obtained in Example 7.

EXAMPLE 14

(R, S)-3-Chloro-1-p-toluenesulfonyloxy-2-propanol (1 gram, 3.78 mmol) and vinyl acetate (0.65 gram, 7.56 mmol) were dissolved in 5 ml of 1,1,1-trichloroethane dried in advance on Molecular Sieve 4A for one day. To the resulting solution was added 1 gram of an enzyme (Amano P: Product of Amano Seiyaku K. K.), and the mixture was stirred at 25° C. and 150 r.p.m. for 8 hours. The reaction mixture was filtered, and the filtrate was subjected to HPLC using an optically active column. It was found that (R)-3-chloro-1-p-toluenesulfonyloxy-2-propanol was obtained in an optical purity of 100% with a theoretical yield of 100%.

EXAMPLE 15

(R, S)-1-phenylethanol (0.276 gram, 2 mmol) and vinyl acetate (0.17 gram, 2 mmol) were dissolved in 10 ml of n-hexane dried in advance on Molecular Sieve 4A for one day. To the resulting solution was added 1 gram of PPL (porcine pancrea lipase: Product of Sigma), and the mixture was stirred at 25° C. and 150 r.p.m. to give (S)-1-phenylethanol in an optical purity of 90% with a theoretical yield of 85%.

EXAMPLE 16

(R, S)-1-Phenyl-2-chloroethanol (0.626 gram, 4.0 mmol) and isopropenyl acetate (0.80 gram, 8.0 mmol) were dissolved in 40 ml of diisopropyl benzene dried in advance on Molecular Sieve 4A for one day. To the resulting solution was added 2 grams of an enzyme. (Amano P: Product of Amano Seiyaku K. K.), and the mixture was stirred at 25° C. and 150 r.p.m. for 10 hours. The reaction mixture was filtered, and the filtrate was subjected to HPLC using an optically active column. (R)-1-phenyl-2-chloroethanol was obtained in an optical purity of 90% with a theroretical yield of 100% and the (S)-acetyl product was obtained in an optical purity of 95% with a theoretical yield of 100%.

What is claimed is:

1. A method for resolving a racemic secondary alcohol into its two antipodes, comprising the steps of:
   reacting a racemic secondary alcohol selected from the group consisting of 2-heptanol, 2-octanol, 2-nonanol, 2-decanol, (R,S)-3-chloro-1-p-toluenesulfonyloxy-2-propanol, (R,S)-1-phenylethanol, (R,S)-1-phenyl-2-chloroethanol, (R,S)-mandelonitrile and phenylethylene glycol with an esterifying agent selected from the group consisting of an acid anhydride and an enol ester of a carboxylic acid in an organic solvent in the presence of a hydrolase to esterify one of the antipodes of the racemic secondary alcohol with the esterifying agent, so that a reaction mixture containing the esterified antipode and unreacted antipode is formed; and
   separating either the esterified antipode or unreacted antipode from said reaction mixture.

2. A method as claimed in claim 1, wherein said acid anhydride is an open-chain or cyclic carboxylic anhydride.

3. A method as claimed in claim 2, wherein said open-chain carboxylic anhydride is a straight-chain or branch-chain symmetric carboxylic anhydride and said cyclic carboxylic acid is a five-membered or 6-membered cyclic carboxylic acid.

4. A method as claimed in claim 2, wherein said cyclic acid anhydride is succinic anhydride, maleic anhydride, phthalic anhydride or glutaric anhydride.

5. A method as claimed in claim 1, wherein said organic solvent is a straight-chain hydrocarbon, a branch-chain hydrocarbon, a halogenated hydrocarbon, an aromatic hydrocarbon, an aliphatic ether or an alicyclic ether.

6. A method as claimed in claim 5, wherein said straight-chained hydrocarbon is n-heptane or n-hexane, said branch-chained hydrocarbon is isobutane, isopentane or 2-methylpentane, said alicyclic hydrocarbon is cyclopentane or cyclohexane, said halogenated hydrocarbon is dichloroethane, trichloroethane, methylene dichloride, chloroform or carbon tetrachloride, said aromatic hydrocarbon is benzene, toluene, xylene, cumene, cymene, mesitylene or diisopropylbenzene, said aliphatic ether is diethyl ether, diisopropyl ether or di-n-butyl ether, and said alicyclic ether is tetrahydrofuran or tetrahydropyrane.

7. A method as claimed in claim 1, wherein said hydrolase is a lipase, an esterase or a protease.

* * * * *